(12) United States Patent
Cook (10) Patent No.: US 8,013,985 B2
(45) Date of Patent: Sep. 6, 2011

(54) METHODS OF MEASURING THE REFRACTIVE INDEX PROFILE OF A TRANSPARENT CYLINDRICAL OBJECT

(75) Inventor: Ian D Cook, Wilmington, NC (US)

(73) Assignee: Corning Incorporated, Corning, NY (US)

( * ) Notice: Subject to any disclaimer, the term of this patent is extended or adjusted under 35 U.S.C. 154(b) by 402 days.

(21) Appl. No.: 12/414,188

(22) Filed: Mar. 30, 2009

(65) Prior Publication Data
US 2010/0245805 A1    Sep. 30, 2010

(51) Int. Cl.
*G01N 21/00* (2006.01)
(52) U.S. Cl. ............ 356/73.1; 356/239.1; 385/12
(58) Field of Classification Search ......... 356/73.1, 356/239.1; 385/12–14, 24, 123–128
See application file for complete search history.

(56) References Cited

U.S. PATENT DOCUMENTS

| | | | |
|---|---|---|---|
| 4,441,811 A | 4/1984 | Melezoglu et al. | 356/128 |
| 4,515,475 A | 5/1985 | Payne et al. | 356/73.1 |
| 4,726,677 A | 2/1988 | Glantschnig et al. | 356/73.1 |
| 4,934,818 A | 6/1990 | Glantschnig et al. | 356/73.1 |
| 5,450,192 A | 9/1995 | Nolf et al. | 356/73.1 |
| 5,463,466 A | 10/1995 | Svendsen | 356/440 |
| 6,574,994 B2 | 6/2003 | Cain et al. | 65/391 |
| 6,611,321 B1 * | 8/2003 | Sasaki | 356/73.1 |
| 2008/0166094 A1 | 7/2008 | Bookbinder et al. | 385/124 |
| 2009/0169163 A1 | 7/2009 | Abbott, III et al. | 385/127 |

OTHER PUBLICATIONS

Glantschnig, W. J., "Index profile reconstruction of fiber preforms from data containing a surface refraction component", Applied Optics, vol. 29, No. 19, Jul. 1, 1990, pp. 2899-2907.
Press, W. H., et al., "Numerical Recipes in C, The Art of Scientific Computing", section of the book entitled, "10.4 Downhill Simplex Method in Multidimensions", Second Edition, published by Cambridge University Press, pp. 408-412.

* cited by examiner

*Primary Examiner* — Tarifur Chowdhury
*Assistant Examiner* — Tara S Pajoohi
(74) *Attorney, Agent, or Firm* — Robert L. Carlson (57) ABSTRACT

Methods of measuring the refractive index profile of a transparent cylindrical object, such as a fiber preform, are disclosed. The methods include transmitting light rays through the cylindrical object in a direction transverse to the central axis at different heights and measuring the deflection angles to define a measured deflection function $\psi_m$. The methods include numerically fitting a target deflection function $\psi_t$ to the measured deflection function $\psi_m$ within a first object region that does not include the object's outer edge. The fit is conducted by varying the yet unknown parameters of the refractive index profile that define the target deflection function to obtain an estimated refractive index profile $\eta^*_i(r)$ over a second object region equal to or greater in size than the first object region. For cylindrical objects having at least one refractive index continuity, the method is applied to the different regions defined by the at least one discontinuity. An example method uses the estimated refractive index profile of a fiber preform to adjust at least one parameter of a preform fabrication process.

20 Claims, 7 Drawing Sheets

METHODS OF MEASURING THE REFRACTIVE INDEX PROFILE OF A TRANSPARENT CYLINDRICAL OBJECT

FIELD

The present invention relates generally to refractive index measurements, and more specifically to methods of measuring the refractive index profile of a transparent cylindrical object such as a fiber preform.

TECHNICAL BACKGROUND

Transparent cylindrical objects, such as fiber preforms, optical fibers, light pipes, light tubes, etc., are used in a variety of optical applications. In many instances, it is desirable to know the refractive index profile of such objects. For example, optical fibers are formed by heating a fiber preform and drawing the molten end into a thin glass thread. The refractive index profile of the preform defines the refractive index profile of the resulting optical fiber, which in turn determines the waveguiding properties of the optical fiber. It is thus important to be able to accurately measure the refractive index profile of the fiber preform.

One technique for measuring the refractive index profile of a transparent cylindrical object utilizes the deflection angle of rays of light emerging from a transversely illuminated object. Typically this involves passing a radiation beam (e.g., a laser beam) through the object in a direction transverse to the object central axis and measuring the resulting beam deflection angles as the laser beam is scanned across the object. The collection of beam deflection angles relative to the input location of the scanned laser beam is commonly known as the "deflection function." Having obtained the deflection function, mathematical methods are then employed to reconstruct the refractive index profile from the measured data. These mathematical methods are generally based on paraxial ray theory, whereby the refractive index profile is determined by applying an inverse Abel transform to the deflection function.

However, the abovementioned technique is not able to provide an accurate measurement of the refractive index profile of a simple homogeneous rod. The reason for this shortcoming is that there is a refractive index discontinuity at the boundary, or edge, of the rod that results in a surface refraction component to the measurement. The publication by Werner J. Glantschnig, entitled "Index profile reconstruction of fiber preforms form data containing a surface refraction component," Applied Optics, Vol. 29, No. 19, Jul. 1, 1990 (the "Glantschnig publication"), which publication is incorporated by reference herein, explains the reasons why a refractive index discontinuity is not accurately reconstructed from the deflection function data.

While the Glantschnig publication proposes a method for measuring the refractive index profile, it requires measuring the deflection angle precisely at the edge of the object, which is difficult to the point of impracticality.

SUMMARY

A first aspect of the methods disclosed herein is a method of measuring a refractive index profile of a transparent cylindrical object having a central axis, a radial coordinate r, an outer edge at a radius r=R, and an actual refractive index profile $\eta_i(r)$ at a wavelength $\lambda$. The method includes transmitting a radiation beam having a wavelength $\lambda$ through the cylindrical object in a direction transverse to the central axis for different heights relative to the central axis. The method also includes detecting positions of the transmitted radiation beam relative to the cylindrical object and converting the positions to corresponding deflection angles to form a measured deflection function $\psi_m$. The method further includes numerically fitting a target deflection function $\psi_t$ to the measured deflection function $\psi_m$ within a first object region that does not include the outer edge by varying yet unknown radius R and yet unknown refractive index $\eta_i$ to obtain an estimated refractive index profile $\eta^*_i(r)$ over a second object region equal to or greater in size than the first object region.

A second aspect of the methods disclosed herein is method of measuring a refractive index profile of a fiber preform having a central axis, a radial coordinate r, an outer edge at a radius r=R, and an actual refractive index profile $\eta_i(r)$ at a wavelength $\lambda$. The method includes transmitting a light beam of wavelength $\lambda$ through the preform in a direction transverse to the central axis for different heights relative to the central axis. The method also includes measuring deflection angles of the transmitted light beam to define a measured deflection function $\psi_m$. The method further includes numerically fitting a target deflection function $\psi_t$ to the measured deflection function $\psi_m$ within a first preform region $R_{FIT}$ that does not include the outer edge, and to within a select tolerance $\delta$ by varying yet unknown radius R and yet unknown refractive index $\eta_i$ to obtain an estimated refractive index profile $\eta^*_i(r)$ over a second preform region equal to or greater in size than the first preform region.

A third aspect of the methods disclosed herein is a method of measuring a refractive index profile of a fiber preform having a central axis, a radial coordinate r, an outer edge at a radius r=R, and an actual refractive index profile $\eta_i(r)$. The method includes generating a measured deflection function comprising discrete data points by transmitting light rays transversely through the preform and measuring corresponding light ray deflection angles. The method also includes identifying respective opposite approximate edges and a center of the measured deflection function, thereby defining first and second halves of the measured deflection function corresponding to first and second halves of the preform. The method further includes defining a first preform region $R_{FIT}$ in the first half of the deflection function that excludes the corresponding preform approximate edge. The method also includes fitting a first target deflection function to the measured deflection function data points within the first preform region by varying the yet unknown radius R and yet unknown refractive index $\eta_i$ to obtain a first estimated refractive index profile and estimated radius for the first half of the preform.

These and other advantages of the invention will be further understood and appreciated by those skilled in the art by reference to the following written specification, claims and appended drawings.

DETAILED DESCRIPTION

Additional features and advantages of the methods briefly described above are set forth in the detailed description that follows, and will be apparent to those skilled in the art from the description or recognized by practicing the methods as described in the following description together with the claims and appended drawings.

In the discussion below, the "refractive index profile" $\eta_i(r)$ is the relationship between refractive index $\eta_i$ and the radial coordinate r. The estimated refractive index profile is $\eta^*_i(r)$ and is the value of the refractive index determined using the methods of the present invention. The normalized radial coordinate r' is defined as r/R, where R is the outer radius of the cylindrical object being measured. Also, the Greek letter $\psi$ is used below for both the deflection angle and the deflection function since these two concepts are closely related. The particular meaning of $\psi$ will be apparent to one skilled in the art from the context of the description.

The description of the present methods is set forth below with reference to a transparent cylindrical object in the form of a fiber preform. However, it will be understood by one skilled in the art that the methods described herein can be applied generally to any cylindrical object having a refractive index profile $\eta_i(r)$ at a given wavelength $\lambda$ of radiation, where the corresponding deflection function can be measured via transverse transmission of the radiation of wavelength $\lambda$ and a target deflection function exists that can be expressed as a function which can be fitted to the measured data.

Figure 1:
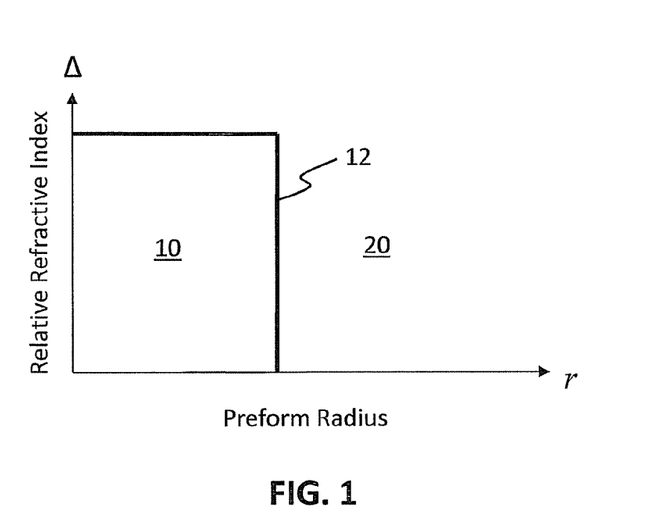
FIG. 1 is a plot of the relative refractive index $\Delta$ versus preform radial coordinate r illustrating an idealized refractive index profile of a homogeneous rod, showing a refractive index discontinuity ("edge") between the rod and the surrounding medium.

FIG. 1 is a plot of the "relative refractive index" $\Delta$ versus radial coordinate r illustrating an idealized refractive index profile of a cylindrical object in the form of a homogeneous rod. The relative refractive index for a homogeneous rod is given by $\Delta(\%)=[\eta_i^2-\eta_o^2)/2\eta_i^2]\times 100$, wherein $\eta_i$ is the refractive index of the rod, and $\eta_o$ is the refractive index of the medium surrounding the rod. The relative refractive index plot of FIG. 1 shows a refractive index discontinuity ("edge") 12 between the rod 10 and the surrounding medium 20.

The Measured Deflection Function

Example embodiments of the methods set forth herein utilize a transverse illumination technique to sample a transparent cylindrical object having an actual refractive index profile $\eta_i(r)$ at an optical wavelength $\lambda$. This illumination technique is based on the principle of refraction wherein a radiation beam (e.g., a light beam or a laser beam) of wavelength $\lambda$ is directed perpendicular to the axis of the transparent cylindrical object. The deflection angle $\psi$ of the transmitted light beam is measured for the given beam height x relative to the central axis of the transparent cylindrical object. To adequately sample the transparent cylindrical object, the incident radiation beam is scanned across the transparent cylindrical object for a number of different heights and the deflection angle $\psi(x)$ for each radiation beam height is measured. This data forms a measured deflection function $\psi_m$ that is then numerically transformed in the manner described below to derive an estimated refractive index profile $\eta^*_i(r)$.

Figure 2:
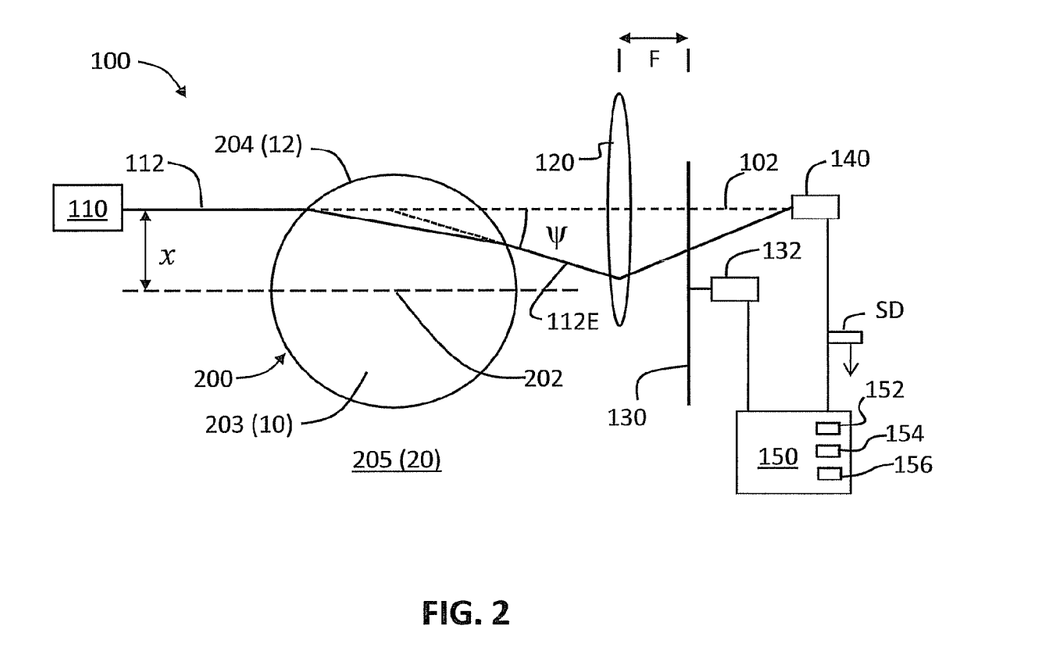
FIG. 2 is a schematic diagram illustrating an example embodiment of a basic deflection function measurement system.

FIG. 2 is a schematic diagram illustrating an example embodiment of a basic deflection function measurement system ("system") 100 that can be used to establish the measured deflection function $\psi_m$. System 100 uses a rotating chopper blade to establish the deflection angle $\psi$. An example measurement system 100 is described in U.S. Pat. No. 4,515,475, which patent is incorporated by reference herein.

System 100 has a system axis 102 and includes a laser source 110 configured to generate a laser beam (or "light beam") 112 along the system axis. System 100 also includes a transform lens 120 arranged along system axis 102 and having a focal length F. A chopper blade 130, which is mechanically connected to a chopper motor 132 so as to be rotationally driven thereby, is arranged at a distance F from transform lens 120. A photodetector unit 140 is arranged along system axis 102 adjacent and downstream of rotating chopper blade 130.

System 100 also includes a controller 150 operably connected to chopper motor 132 and photodetector unit 140. Controller 150 is, for example, a computer that includes a processor unit ("processor") 152 (e.g., a CPU), a memory unit 154 and support circuitry 156 all operably interconnected. Processor 152 may be or include any form of a general purpose computer processor that can be used in an industrial setting. Memory unit 154 comprises a computer-readable medium capable of storing instructions (e.g., software) that direct processor 152 to carry out the methods as described in detail below. Memory unit 154 may be, for example, random-access memory, read-only memory, floppy or hard disk drive, or other form of digital storage. In an example embodiment, the instructions stored in memory unit 154 are in the form of software that, when executed by processor 152, transforms the processor into a specific-purpose processor that controls (i.e., directs or causes) system 100 to carry out one or more of the methods described herein. Support circuitry 156 is operably (e.g., electrically) coupled to processor 152 and may comprise cache, clock circuits, input/output sub-systems, power supplies, control circuits, and the like.

A transparent cylindrical object in the form of a fiber preform ("preform") 200 having a refractive index profile $\eta_i(r)$ to be measured is arranged between laser 110 and transform lens 120. Preform 200 has a central axis 202 and includes a preform body 203 having outer surface or outer "edge" 204 that defines an outer preform radius R. An outside region 205 surrounds preform body 203. In an example embodiment, outside region 205 comprises aforementioned surrounding medium 20 and preform body 203 comprises aforementioned homogeneous rod region 10.

While preform 200 is typically placed in a measurement cell to facilitate the deflection angle measurement, the measurement cell is omitted in system 100 of FIG. 2 for ease of illustration, and is described in greater detail below in connection with a more detailed embodiment of a deflection function measurement system.

In the operation of system 100, preform 200 is arranged within system 100 so that no portion of the preform intersects system axis 102. Laser beam 112 initially travels parallel to system axis 102, through lens 120, chopper blade 130, and onto photodetector 140 without intersecting preform 200, thereby establishing a baseline for the measurement. Thereafter, preform 200 is moved (e.g., scanned), or the laser 110, lens 120, chopper blade 130 and photodetector 140 are all simultaneously moved (e.g., scanned) so that the laser beam height x can be varied in order to send the laser beam through different parts of preform 200.

Laser beam 112 is first incident on preform outer edge 204 and undergoes a first refraction. The first-refracted laser beam 112 then travels through preform 200 and exits the preform on the opposite side ("opposite edge"), where it undergoes a second refraction and becomes "exit" laser beam 112E. The deflection angle $\psi$ is defined by the path of exit laser beam 112E relative to the direction of the incident laser beam. Exit laser beam 112E then passes through transform lens 120 and rotating chopper blade 130, and is detected by photodetector unit 140. Photodetector unit 140 then sends a corresponding detector signal SD to controller 150 for processing.

The placement of chopper blade 130 a distance F away from transform lens 120 makes the position where exit laser beam 112E intersects chopper blade 130 proportional to the deflection angle $\psi$. By performing measurements of the deflection angle $\psi$ over a range of laser beam heights x, the corresponding detector signals SD received and processed by controller 150 (using the measured timer counts for rotating chopper blade 130) create the measured deflection function $\psi_m$, as described in greater detail below.

Figure 3:
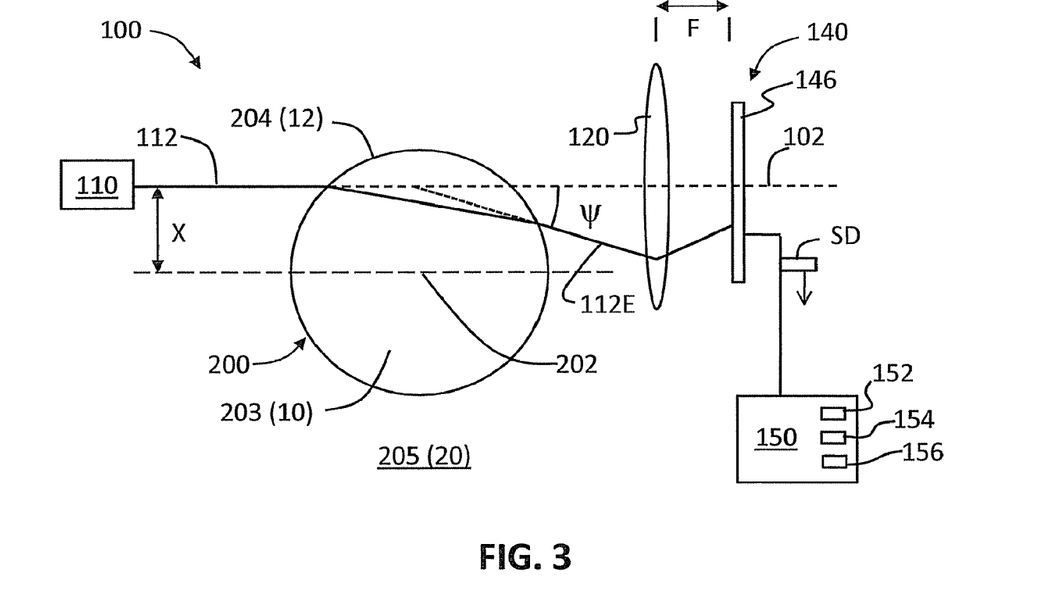
FIG. 3 is a schematic diagram similar to FIG. 2 and illustrating another example embodiment of a basic deflection function measurement system that utilizes a charge-coupled device (CCD) array.

FIG. 3 is a schematic diagram similar to FIG. 2 and illustrates another example embodiment of system 100. System 100 of FIG. 3 eliminates the need for chopper blade 130 and chopper motor 132 by providing photodetector unit 140 in the form of a charge-coupled-device (CCD) array detector ("CCD array") 146. CCD array 146 is placed a distance F behind transform lens 120 and thus directly records the position and intensity of exit light beam 112E. The benefit of using the CCD-array-based system 100 of FIG. 3 is that the measured deflection function $\psi_m$ can be captured in a much shorter time period than is possible with the chopper based system 100 of FIG. 2.

Many other deflection function measurement systems similar to those described above can be used to obtain the deflection function $\psi$. Some examples are described in U.S. Pat. Nos. 4,441,811; 4,726,677; 4,934,818; and 5,450,192, which patents are incorporated by reference herein.

Figure 4:
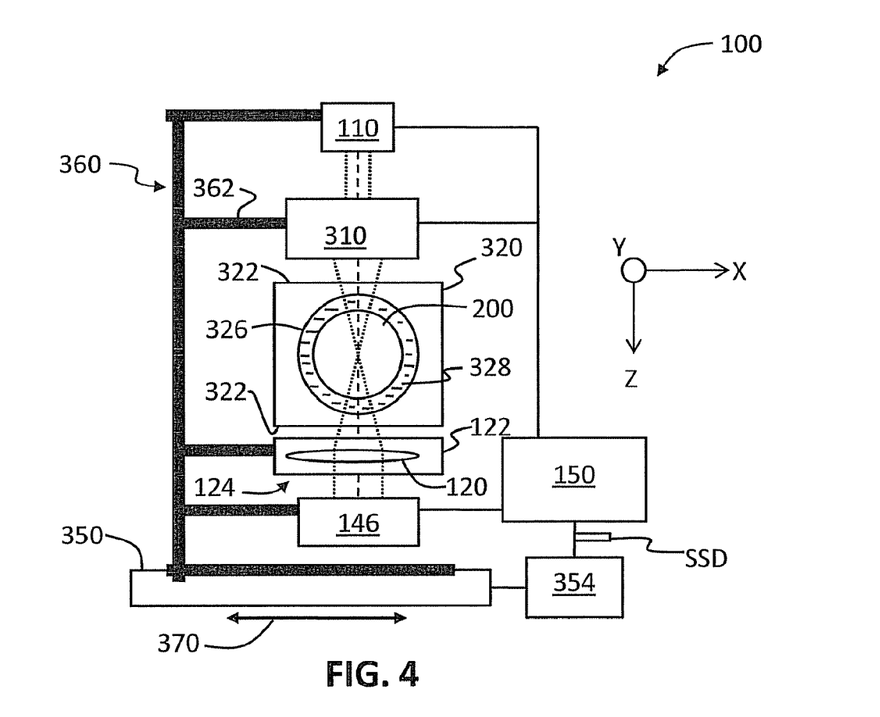
FIG. 4 is a more detailed schematic diagram of an example CCD-based deflection function measuring system.

FIG. 4 is a more detailed schematic diagram of an example CCD-based deflection function measuring system 100. Cartesian X-Y-Z coordinates are shown for the sake of reference. System 100 of FIG. 4 is based on the system shown in FIG. 3 and further includes beam-conditioning optics 310 arranged immediately adjacent and downstream of laser 110. Beam-conditioning optics 310 are configured to focus laser beam 112 so that the beam focus is within preform body 203. Transform lens 120 now resides in a transform lens holder 122, thereby forming a transform lens assembly 124.

A measurement cell 320 is arranged in between beam-conditioning optics 310 and transform lens assembly 124. Measurement cell 320 has opposite sides 322 that are planar and at right-angles to system axis 102 so that laser beam 112 is normally incident thereon. Measurement cell 320 has an interior region 326 sized to accommodate preform 200 along with an index-matching fluid 328. An example measurement cell is disclosed in U.S. Pat. No. 5,463,466, which patent application is incorporated by reference herein. In an example embodiment, index-matching fluid 328 has a refractive index that substantially matches the refractive index of measurement cell 320 and together they form surrounding or outside region 205 (FIG. 3).

System 100 of FIG. 4 also includes a movable translation stage 350 operably connected to a stage driver 354, which in turn is operably coupled to controller 150. In an example embodiment, translation stage 350 is an air bearing stage. A frame 360 is supported on translation stage 350. Frame 360 supports laser 110, beam-conditioning optics 310, transform lens assembly 124, and CCD array 146 in the above-described configuration along system axis 102 via respective support members 362. Measurement cell 320 (along with preform 200 and index matching fluid 328 contained therein) is held in a fixed position between beam-conditioning optics 310 and the transform lens assembly 124 by a measurement system holder (not shown).

The operation of system 100 of FIG. 4 is similar to that of system 100 of FIG. 3, and further includes controller 150 sending a control signal SSD to stage driver 354 to move translation stage 350 in the +X or −X, which serves to move frame 360 and the components supported thereby, as indicated by double arrow 370. The movement of frame 360 allows for the laser beam height x (FIG. 3) to be varied relative to measurement cell 320 so that the measured deflection function $\psi_m$ includes a range of radii of preform 200.

To establish the measured deflection function $\psi_m$, the measured pixel locations Of exit laser beam 112E for the CCD-based system 100 of FIG. 2 are converted (e.g., by processor 152) from an array of measured positions to an array of deflection angles $\psi$.

Determining the Refractive Index Profile

Once the measured deflection function $\psi_m$ is established and stored in memory unit 154, the next step is to calculate the refractive index profile $\eta_i(r)$—or more specifically, an estimated refractive index profile $\eta^*_i(r)$ that is closely representative of the actual refractive index profile $\eta_i(r)$. The calculation is preferably carried out in processor 152 based on instructions stored in memory unit 154, which instructions correspond to one or more of the numerical methods described below.

In an example embodiment, a symmetry correlation is carried out on measured deflection function $\psi_m$ to define a center coordinate. The measured deflection function $\psi_m$ is then split into two halves about this center coordinate, and a refractive index half-profile is calculated for each of the two halves, as described below. The resulting estimated index profiles $\eta^*_i(r)$ for each of the two halves are then combined (e.g. averaged) to obtain a final estimated refractive index profile.

Figure 5:
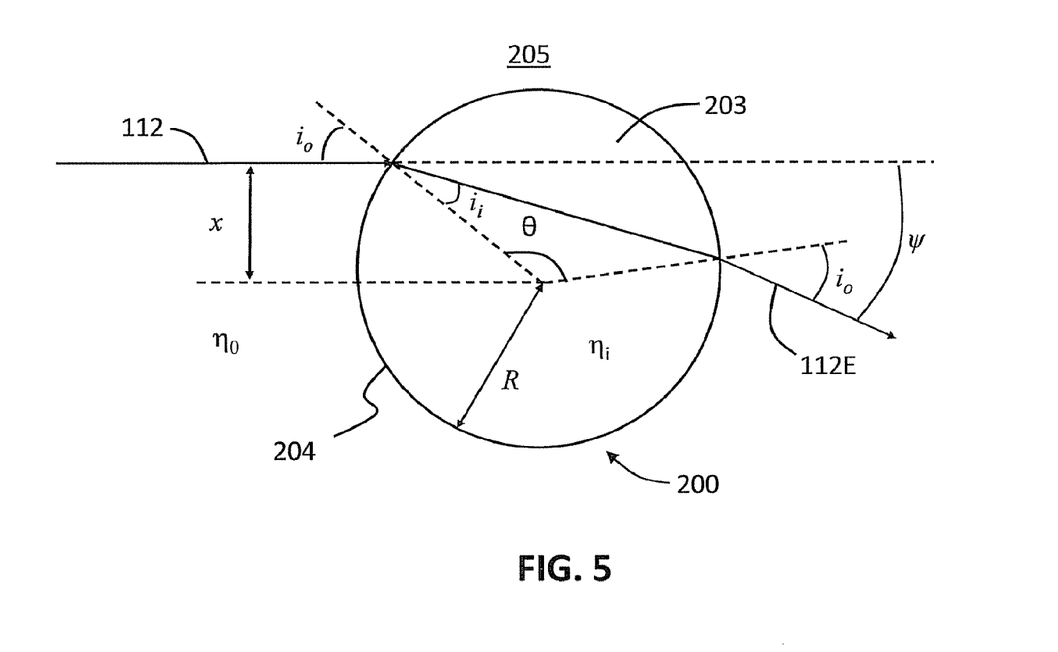
FIG. 5 is a schematic diagram of a cylindrical preform as viewed end on, and showing the relevant parameters for the refractive index profile calculation.

The steps for calculating the estimated refractive index profile $\eta^*_i(r)$ are now discussed in connection with a preform 200 having a constant refractive index $\eta_i(r)=\eta_i$ as is the case for the homogeneous rod. FIG. 5 is a schematic diagram of such a cylindrical preform 200 as viewed end on. FIG. 5 shows the relevant parameters for the refractive index profile calculation, namely preform radius R, the constant refractive index $\eta_i$ of preform body 203, and refractive index $\eta_o$ of surrounding homogeneous region (medium) 205. In addition, $i_o$ is the angle of incidence of laser beam 112, $i_i$ is the angle of refraction within preform body 203, and x is the height of the laser beam relative to preform central axis 202. In addition, θ measures the angle between radial lines that extend from the center of preform 200 out to the points on preform edge 204 where laser beam 112 enters and exits the preform.

Application of Snell's law to light ray 112 in FIG. 5 yields the following relationship:

$$\eta_o \sin(i_o) = \eta_i \sin(i_i) \quad (1)$$

The geometry of FIG. 5 provides the following relationship for the incident angle $i_o$:

$$i_o = \arcsin\left(\frac{x}{R}\right). \quad (2)$$

Combining equations (1) and (2) yields the following expression for the angle of refraction:

$$i_i = \arcsin\left(\frac{\eta_o}{\eta_i} \cdot \frac{x}{R}\right) \quad (3)$$

For a constant refractive index $\eta_i$, the ray paths are straight lines, so that the internal angle θ is given by:

$$\theta = \pi - 2i_i \quad (4)$$

The deflection angle ψ of light ray 122 is thus given by $$\psi = 2(i_i - i_o), \quad (5)$$

so that the deflection function ψ(x) has the following mathematical form:

$$\psi(x) = 2\left[\arcsin\left(\frac{\eta_o}{\eta_i}\frac{x}{R}\right) - \arcsin\left(\frac{x}{R}\right)\right] \quad (6)$$

Figure 6:
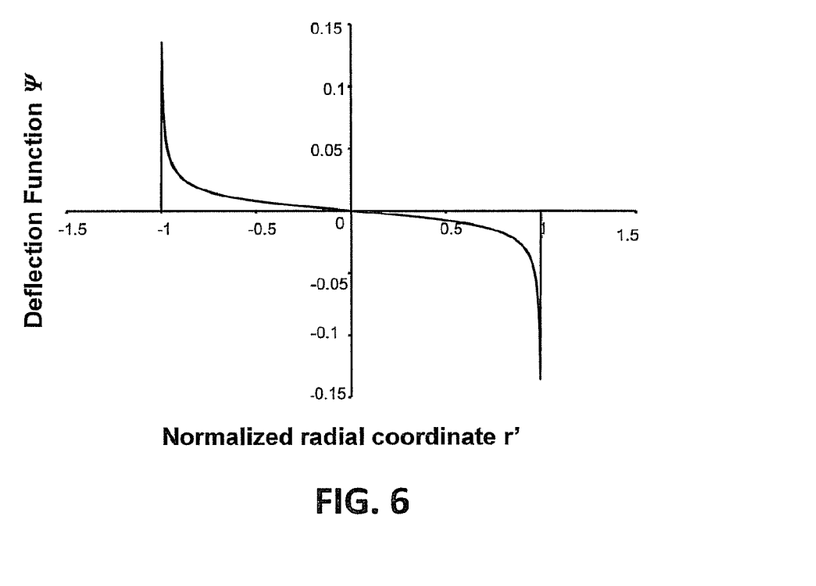
FIG. 6 is a plot of the deflection function $\psi$ of equation (6) as a function of the normalized preform radial coordinate r'.

In the paraxial case, where the deflection angles ψ are small, the laser beam height x is considered equal to the radial coordinate r. In the following discussion, x and r are considered to be interchangeable. FIG. 6 is a plot of the deflection function ψ of equation (6) as a function of the normalized preform radius r'=r/R for a homogeneous rod where $\eta_i - \eta_o = 0.01$. Note the steep edges to the plot where r'=−1.0 and 1.0.

Estimating the refractive index profile $\eta^*_i(r)$ from the measured deflection function $\psi_m$ involves a number of steps. The first step involves finding edges of the measured deflection function $\psi_m$ that correspond to the actual outer edge 204 of preform 200. As described above, the measurement data consists of a set of discrete data points, and therefore the edge positions do not typically exactly coincide with the exact edge positions of the preform, and so are referred to as "approximate edges." For ease of illustration, only a single edge is examined in detail since the procedure is the same for both edges. Note that cylindrical preform 200 actually includes a single circular "edge," but this edge is considered as being made of two sections (e.g., front and back halves) for the purposes of the calculation.

Figure 7:
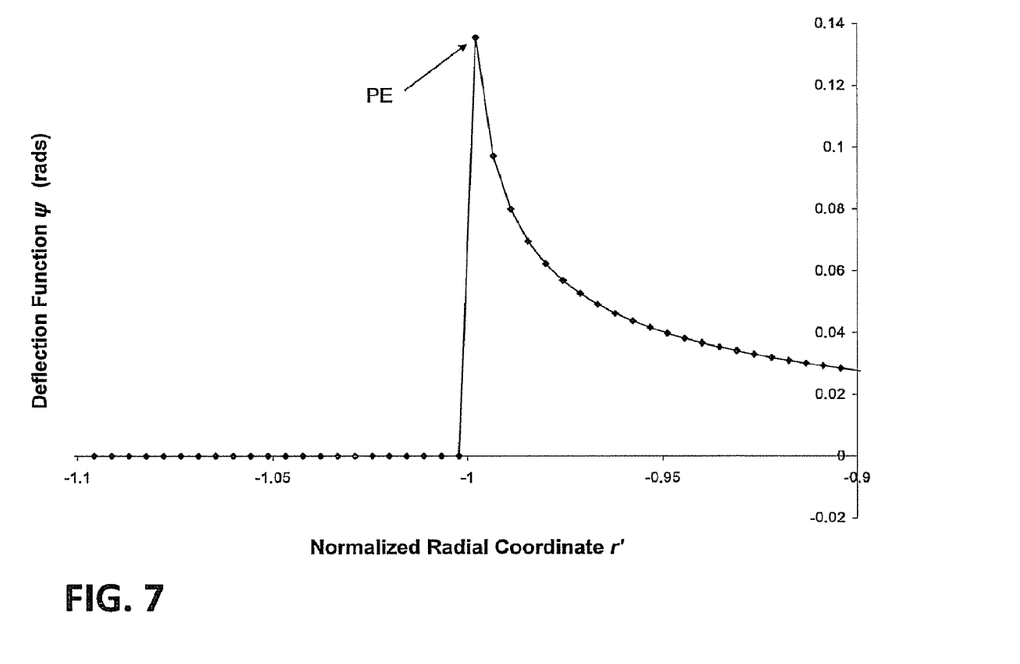
FIG. 7 is a plot of the data points for the measured deflection angle $\psi$ versus the normalized preform radial coordinate r' for a portion of an example measured deflection function $\psi_m$.

FIG. 7 is a plot of the discrete data points for the measured deflection angle ψ versus the normalized preform radius r' for a portion of an example measured deflection function $\psi_m$.

Note that there is no measured data point that coincides with the exact outside edge of the preform, i.e., directly at normalized preform radius r'=−1.0.

There are a number of ways in which approximate edges can be located, and the methods of the present invention are not particularly sensitive to the method used. In an example embodiment, the position of an approximate edge is defined as that point where the deflection function has a maximum rate of change, i.e. the point associated with the highest gradient.

Once the approximate edge locations of the measured deflection function $\psi_m$ are determined, the next step is to select a preform (object) region $R_{FIT}$ of preform (object) 200 over which to apply the fit of a target deflection function $\psi_t$ to the measured deflection function $\psi_m$. In the case of the homogeneous rod, equation (6) describes the target deflection function $\psi_t$. It is generally preferred to avoid applying the fit too close to the actual edge 204 of preform 200 because the finite size of laser beam 112 can lead to incomplete sampling the inside of the preform at this location. It is noted here that, unlike prior art methods that require precise edge locations, the present method locates the edge ostensibly to ensure that the fit is performed away from the approximate edge locations.

Figure 8:
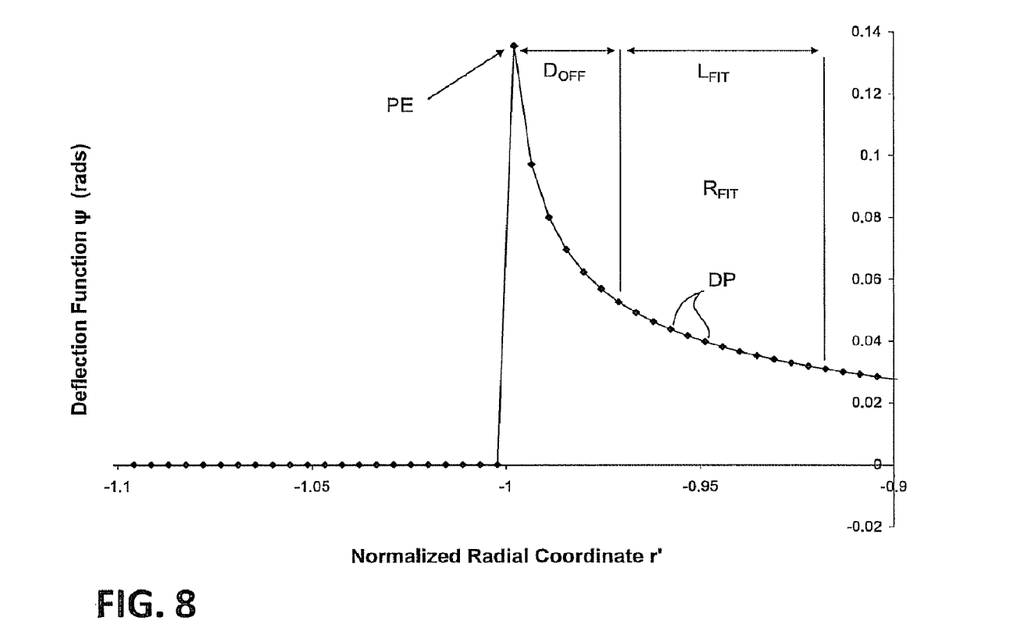
FIG. 8 is the same plot of FIG. 7, but shows the approximate edge point PE, a fit-offset distance $D_{OFF}$ from preform outer edge 204, and a fit region $R_{FIT}$ within the preform and having a fit length $L_{FIT}$.

FIG. 8 is the same plot as FIG. 7, but shows the approximate edge point PE, a fit offset distance $D_{OFF}$ from preform outer edge 204, and fit region $R_{FIT}$ within preform 200. Fit region $R_{FIT}$ has a fit length $L_{FIT}$. The data fit for the target deflection function $\psi_t$ is applied to those data points DP of the measured deflection function $\psi_m$ that fall within fit region $R_{FIT}$. Thus, in an example embodiment of the method, the selected fit region $R_{FIT}$ does not include the actual or approximately located preform edge 204.

Figure 9:
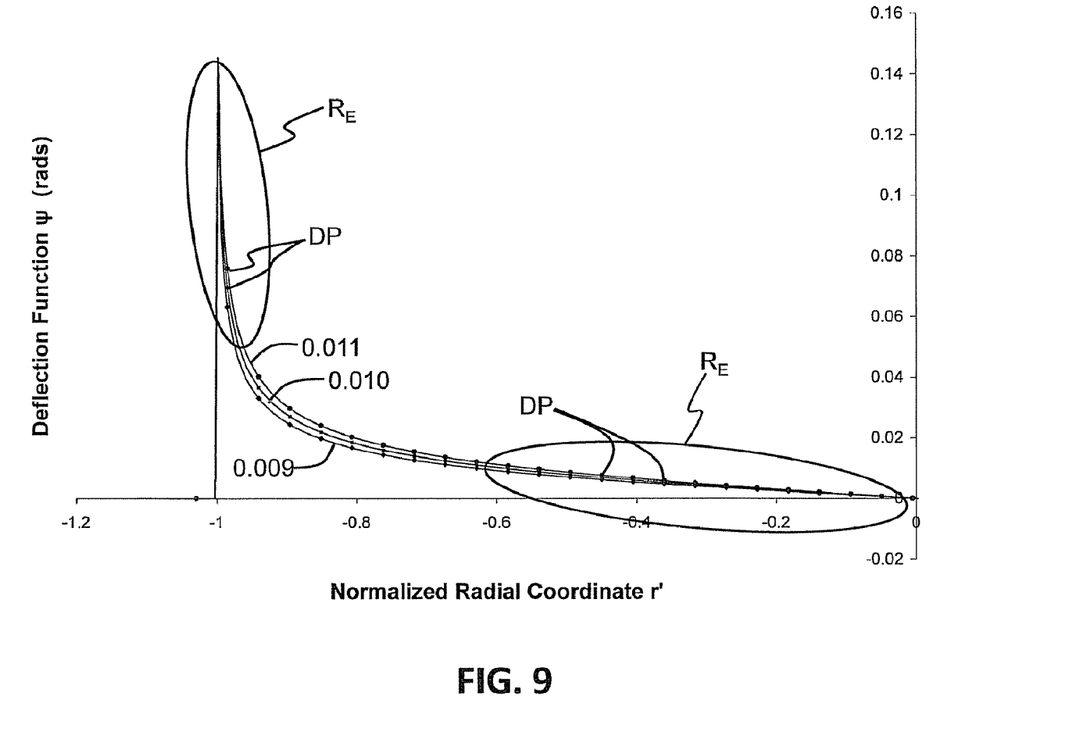
FIG. 9 is a plot of three deflection functions versus the normalized preform radial coordinate r' for three different step changes in the preform refractive index, and which shows example preform exclusion regions RE that are typically excluded from the fitting process.

On the other hand, it is generally preferred not to try to extend fit region $R_{FIT}$ too far from preform outer edge 204 because, as can be seen from the plot of FIG. 6, the measured deflection function $\psi_m$ starts to flatten out quite rapidly towards the preform central axis 202, meaning that the data points in this region add less uniqueness to the fit to the target deflection function $\psi_t$. This is further illustrated in the plot of FIG. 9, which shows the deflection functions of equation (6) for values of $\eta_i - \eta_o = 0.011$ and $\eta_i - \eta_o = 0.009$ plotted alongside the original deflection function for $\eta_i - \eta_o = 0.01$. The curves become less distinct in the region just inside preform edge 204, for example r'≧0.98, and also in the central preform region 0≦r'≦0.5. Thus, in exemplary embodiments, fit region $R_{FIT}$ is within the range 0.5≦r'≦0.98, or more preferably within the range 0.75≦r'≦0.98. Also in an exemplary embodiment, $D_{OFF}$ is about (0.2)·r'. FIG. 9 also illustrates for the sake of completeness exemplary exclusion regions $R_{EX}$ outside of fit region $R_{FIT}$, for which the data points DP residing therein are generally not included in the fit calculation.

Once fit region $R_{FIT}$ is selected, the deflection function ψ of equation (6) is used as a target deflection function $\psi_t$ to find the best fit to the data of the measured deflection function $\psi_m$ based on selecting the yet unknown values $\eta_i$ and R. The result of the fitting process yields the estimated refractive index profile $\eta^*_i$ for the actual refractive index profile, and an estimated value R* for the actual preform outer radius R. In an exemplary embodiment, the the estimated refractive index profile $\eta^*_i$ is obtained over a preform (object) region that is equal to or greater in size than fit region $R_{FIT}$. For example, the estimated refractive index profile $\eta^*_i$ is defined over a preform (object) region beyond one of the above-defined ranges for the fit region $R_{FIT}$, and in one exemplary embodiment extends over the range 0≦r'≦1.

An example fitting process employs a multidimensional minimization method, such as the "downhill simplex method" of Nelder and Mead, as described in the article, Nelder J. A. and Mead R. 1965, Computer Journal vol. 7, pp. 308-313, and in the section of the book by William H. Press et al., entitled "Numerical Recipes in C, The Art of Scientific Computing," Second Edition, by published by Cambridge University Press, on pages 408-412, which article and book section are both incorporated herein by reference.

The minimization method requires formulating a function for which the minimum of that function is the desired outcome. In an exemplary case, this function can be formulated as an error function Err of the fit of the target deflection function $\psi_t$ to the data of the measured deflection function $\psi_m$, generally described by the equation Err=$\psi_m$−$\psi_t$.

In an exemplary embodiment, the methods described herein use the "sum-of-the-square of the differences" in formulating this function, namely:

$$Err = \sum_{n=1 to FitLength} \left(\psi_{m_n} - 2\left[\arcsin\left(\frac{\eta_o}{\eta_i}\frac{x}{R}\right) - \arcsin\left(\frac{x_n}{R}\right)\right]\right)^2 \quad (7)$$

The Nelder-Mead minimization method iterates through choices for $\eta^*_i$ and $R^*$ until the solution (i.e., the difference between the target and measured deflection functions $\psi_t$ and $\psi_m$) converges to within an acceptable limit (tolerance) $\delta$. To this end, it is necessary to provide starting conditions for the iteration process and step movements (i.e. the amount by which a parameter can change between iterations).

In an example embodiment, the starting conditions include the approximate edge location of preform 200 for a preform of radius R, and an expected value for the refractive index $\eta_i$ based on knowledge of how the preform was made and the target refractive index for the preform. Example step movements for the numerical iteration include 0.0001 for the radius and 0.000001 for the index. An exemplary convergence tolerance is $\delta \leq 1 \times 10^{-15}$, and an example maximum number of iterations is 1,500. One skilled in the art will appreciate that these example step movements and convergence tolerance can be varied to suit the particular set of data being used, the particular refractive index profile being considered, and/or the desired accuracy of the calculation.

It is possible for a numerical multidimensional minimization routine to not always terminate at the global minimum for the selected function. Thus, in an example embodiment of the present methods, once a solution is found, the fit is restarted from somewhere close to the initial solution and allowed to run again. In cases where the calculation is not time critical, in an example embodiment the fit is run a number of times (e.g. five times), and the result obtained for the last run is considered to be the final solution.

Preforms With More Than One Refractive Index Discontinuity

Whereas the methods described above have been applied to the case of a homogeneous rod and is most beneficial for those refractive index profiles that contain a refractive index discontinuity, the most general case to which the methods apply also includes profiles that do not contain a refractive index discontinuity.

The method as described above also applies to preforms having more than one refractive index discontinuity, or region. For such preforms, the above methods are normally applied sequentially to the different regions in turn, although if a suitable deflection function expression is available, the methods can also be applied by treating the profile as a single region.

Figure 10:
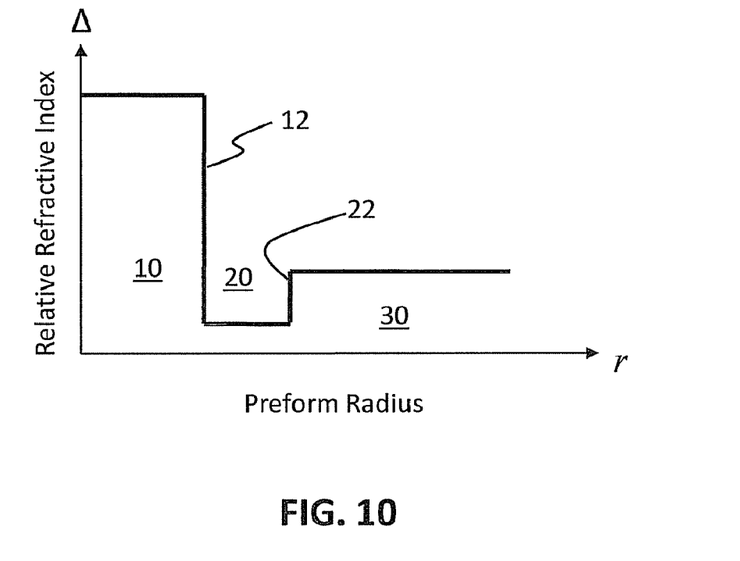
FIG. 10 is a plot of relative refractive index $\Delta$ versus preform radial coordinate r illustrating an idealized refractive index profile for a preform with two step changes in refractive index.

The plot of FIG. 10 shows a (relative) refractive index profile having two step index changes at interfaces 12 and 22 that define the core 10, moat 20 and cladding 30. It is noted here that cladding region 30 is typically added to the preform after refractive index profile measurements are performed on central core 10 and moat 20.

A refractive index profile with more than one discontinuity is typically handled, for example, by working from the outside edge 204 of preform 200 in towards central axis 202. This involves finding the solution for the outermost refractive index region (e.g., moat 20), subtracting the measured deflection function $\psi_m$ for this region from the full measured deflection function, and carrying out the above-described method for the adjacent inner refractive index region (e.g., core 11).

Figure 11:
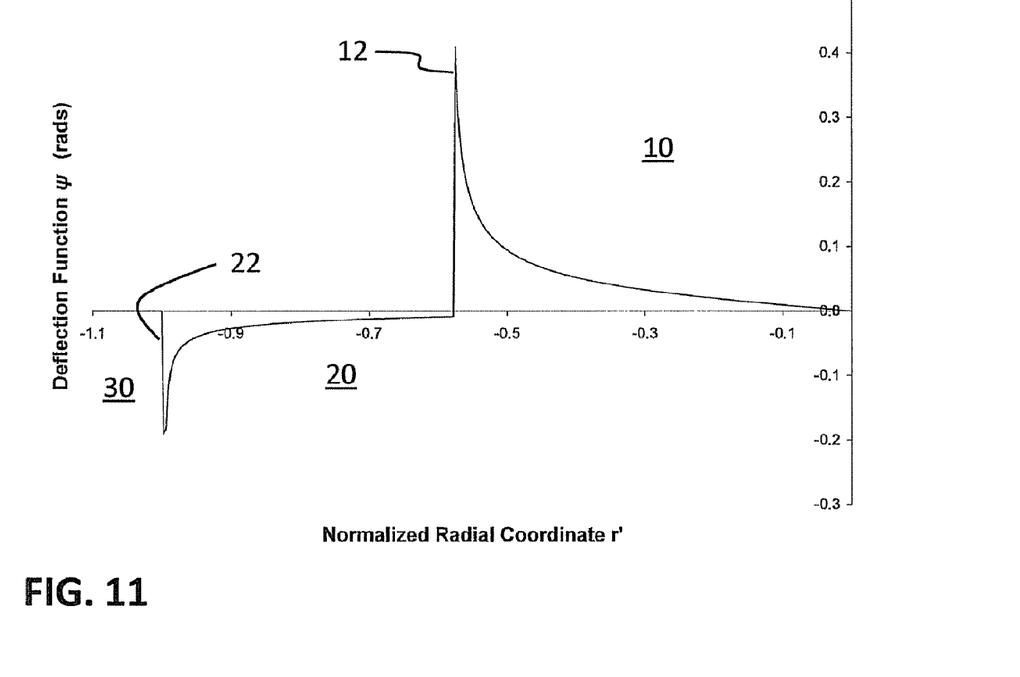
FIG. 11 is a plot of a portion of the deflection function for the refractive index profile of FIG. 10.
Figure 12:
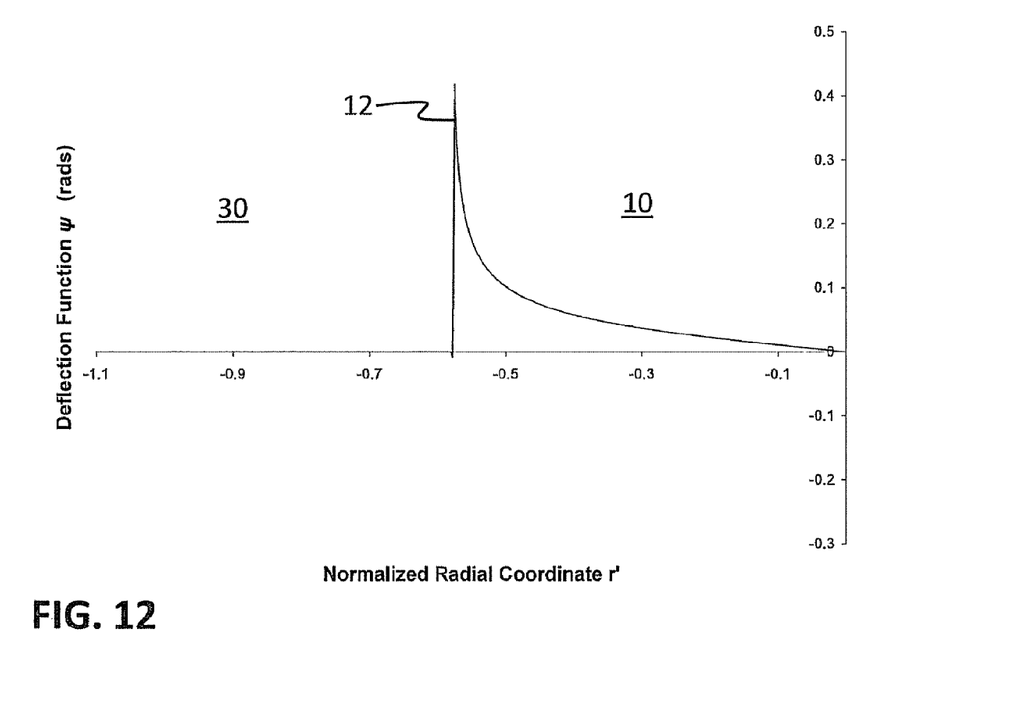
FIG. 12 is the same as FIG. 11, but shows the deflection function after the present method has been applied to the first step change in refractive index and the resultant fitted deflection function removed.

The plot of FIG. 11 shows the deflection function for the refractive index profile of FIG. 10 Applying the present methods to this deflection function, moat 20 is the first region that is processed. Having found the fitted target deflection function $\psi_t$ for moat 20, this is then subtracted from the measured deflection function $\psi_m$, resulting in a new deflection function as shown in FIG. 12. This new deflection function is then processed by a second application of the same method.

In demonstrating how the method can be applied to a refractive index profile with more than one refractive index discontinuity, it will be apparent to one skilled in the art that this same method can be applied to a more generalized preform refractive index profile where one or more of the outer regions of the preform contain an index discontinuity, but the inner region, or regions, do not. In this case, the method described herein is applied to those regions where the refractive index discontinuity is present and the aforementioned prior art, or other suitable reconstruction method, is then applied to the remainder of the deflection function.

Comparison to Prior Art Method

As discussed above, the prior art methods are not particularly accurate because of the surface refraction component, and because they are crucially dependent on deflection angle measurements made at outer edge 204 of preform 200. Not having a measurement data point that precisely samples the very edge of the preform results in a significant loss in effectiveness of the various prior art approximations.

To demonstrate the robustness of the methods described herein as compared to the prior art methods, a refractive index profile having a positive step change in refractive index of $\Delta\eta$=+0.024 was modeled using Zemax Optical CAD software, available from Zemax Development Corporation, Bellevue, Wash. This step-index profile represents the largest step change in index considered in the Glantschnig publication.

Figure 13:
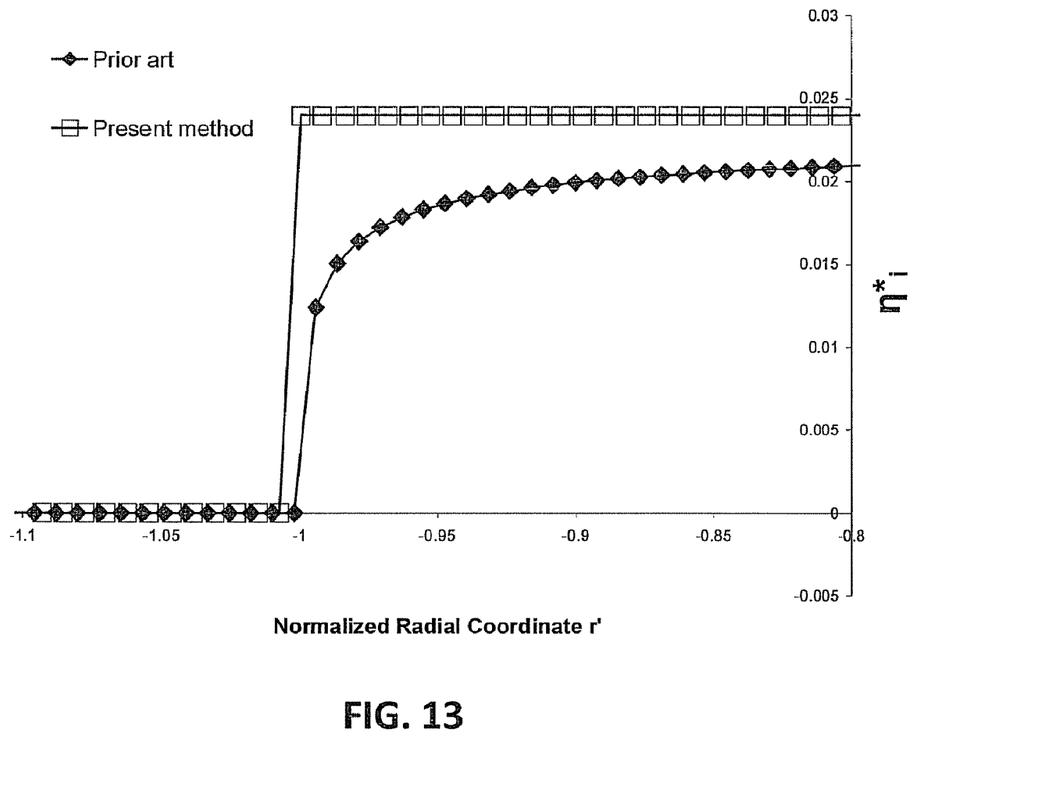
FIG. 13 plots the estimated refractive index profile $\eta^*_i(r)$ versus the preform radial coordinate r, as calculated using the present method (open squares), along and with the prior art method of the Glantschnig publication (closed diamonds).

FIG. 13 plots the estimated refractive index profile $\eta^*_i$ as calculated using the methods of the present invention (open squares) along and with the method set forth in prior art of the Glantschnig publication (closed diamonds). As can be seen from FIG. 13, the present method results in an estimated refractive index profile $\eta^*_i$ that much more closely matches the actual step-function refractive index profile. In addition, the present method is able to provide a more precise measure of the radius R of the preform since the estimated radius $R^*$ is one of the parameters of the fit.

Feedback to Preform Fabrication Process

Example methods of making preform 200 include employing various deposition techniques, such as Outside Vapor Deposition (OVD), Vapor Axial Deposition (VAD), Modified Chemical Vapor Deposition (MCVD) and Plasma Chemical Vapor Deposition (PCVD). Various methods of forming preforms using these techniques are described in U.S. Pat. No. 6,574,994, which patent is incorporated by reference.

By way of example, the MCVD process typically involves passing oxygen and gas vapors containing Si (e.g., $SiCl_4$) and Ge (i.e., $GeCl_4$) to the inside of a heat-resistant glass tube and applying heat to the tube to cause the formation of $SiO_2$ and $GeO_2$ on the cylinder walls. The glass tube is rotated to uniformize the deposition of the $SiO_2$ and $GeO_2$, which fuse to form glass within the tube. The actual refractive index profile rid and preform radius R depend on a number of system parameters, which include the timing and relative flow rates of the Si-containing and Ge-containing gas vapors, the amount of heat applied to the glass tube when forming $SiO_2$ and $GeO_2$, the oxygen flow rate, and the rotation speed of the glass tube, and so on.

Thus, the present methods optionally include using at least one of the estimated values $\eta^*_i$ and $R^*$ to adjust at least one parameter in the preform fabrication process to reduce the difference between an expected refractive index profile and/or the preform radius and their corresponding estimated values. Since the estimated values $\eta^*_i$ and $R^*$ provide insight as to what parameters need to be adjusted to create a preform having the expected refractive index profile, this feedback step reduces the amount of time it takes to fabricate preforms within the target specifications.

It is to be understood that the foregoing description is exemplary of the inventive methods and is only intended to provide an overview for the understanding of the nature and character of the methods as they are defined by the claims. The accompanying drawings are included to provide a further understanding of the methods and are incorporated into and constitute part of this specification. The drawings illustrate various features and embodiments of the methods which, together with their description, serve to explain the principals and operation of the methods. It will become apparent to those skilled in the art that various modifications to the preferred embodiments of the methods as described herein can be made without departing from the spirit or scope of the methods as defined by the appended claims.

What is claimed is:

1. A method of measuring a refractive index profile of a transparent cylindrical object having a central axis, a radial coordinate r, an outer edge at a radius r=R and an actual refractive index profile $\eta_i(r)$ at a wavelength $\lambda$, the method comprising:
    transmitting a radiation beam having a wavelength $\lambda$ through the cylindrical object in a direction transverse to the central axis for different heights relative to the central axis;
    detecting positions of the transmitted radiation beam relative to the cylindrical object and converting the positions to corresponding deflection angles to form a measured deflection function $\psi_m$; and
    numerically fitting a target deflection function $\psi_t$ to the measured deflection function $\psi_m$ within a first object region that does not include the outer edge by varying yet unknown radius R and yet unknown refractive index $\eta_i$ to obtain an estimated refractive index profile $\eta^*_i(r)$ over a second object region equal to or greater in size than the first object region.

2. The method according to claim 1, wherein the cylindrical object comprises a fiber preform.

3. The method according to claim 1, wherein the actual refractive index profile has at least one step change that defines adjacent object regions having different refractive indices, and including performing said numerical fitting for each object region.

4. The method according to claim 1, including immersing the cylindrical object in an index matching oil that substantially matches a refractive index of an outer portion of the cylindrical object adjacent the outer edge.

5. A method of measuring a refractive index profile of a fiber preform having a central axis, a radial coordinate r, an outer edge at a radius r=R, and an actual refractive index profile $\eta_i(r)$ at a wavelength $\lambda$, the method comprising:
    transmitting a light beam of wavelength $\lambda$ through the preform in a direction transverse to the central axis for different heights relative to the central axis;
    measuring deflection angles of the transmitted light beam to define a measured deflection function $\psi_m$; and
    numerically fitting a target deflection function $\psi_t$ to the measured deflection function $\psi_m$ within a first preform region $R_{FIT}$ that does not include the outer edge, and to within a select tolerance $\delta$ by varying yet unknown radius R and yet unknown refractive index $\eta_i$ to obtain an estimated refractive index profile $\eta^*_i(r)$ over a second preform region equal to or greater in size than the first preform region.

6. The method according to claim 5, wherein said numerically fitting includes performing a multi-dimensional minimization that uses a sum-of-the-square of differences between the target deflection function $\psi_t$ and the measured deflection function $\psi_m$.

7. The method according to claim 5, further including:
    finding an approximate edge of the measured deflection function $\psi_m$; and
    excluding the approximate edge from the select first preform region.

8. The method according to claim 7, wherein finding the approximate edge includes identifying a radial position wherein the measured deflection function has a maximum rate of change.

9. The method according to claim 7, wherein the preform has a normalized radial coordinate r'=r/R and wherein the first region is located a distance $D_{OFF}$ from the approximate edge, wherein $D_{OFF}$ is about $(0.2) \cdot r'$.

10. The method according to claim 5, wherein the preform has a normalized radial coordinate r'=r/R, and wherein the first preform region $R_{FIT}$ is within the range $0.5 \leq r' \leq 0.98$.

11. The method according to claim 5, wherein the actual refractive index profile has at least one step change that defines adjacent preform regions having different refractive indices, and including performing said numerical fitting for each preform region.

12. The method according to claim 5, including immersing the fiber preform in an index-matching fluid that substantially matches an index of refraction of an outer region of the preform adjacent the preform outer edge.

13. The method according to claim 5, wherein measuring the deflection angles includes making spatial measurements of the transmitted light rays with a photodetector and converting the spatial measurement into angular measurements.

14. The method of claim 5, wherein said numerical fitting is performed in a computer having a computer readable medium and a processor, wherein the computer readable medium has instructions embodied therein that, when executed by the processor, cause the processor to perform said numerical fitting.

15. The method according to claim 5, wherein the measured preform is a first preform fabricated using a preform fabrication process intended to generate an expected refractive index profile, the method further including:
    measuring a difference between the estimated refractive index profile and the expected refractive index profile; and
    adjusting at least one parameter of the preform fabrication process to reduce said difference in a second preform fabricated by the fabrication process.

16. A method of measuring a refractive index profile of a fiber preform having a central axis, a radial coordinate r, an outer edge at a radius r=R, and an actual refractive index profile $\eta_i(r)$, the method comprising:
    a) generating a measured deflection function comprising discrete data points by transmitting light rays transversely through the preform and measuring corresponding light ray deflection angles;
    b) identifying respective opposite approximate edges and a center of the measured deflection function, thereby defining first and second halves of the measured deflection function corresponding to first and second halves of the preform;
    c) defining a first preform region $R_{FIT}$ in the first half of the deflection function that excludes the corresponding preform approximate edge; and
    d) fitting a first target deflection function to the measured deflection function data points within the first preform region by varying the yet unknown radius R and yet unknown refractive index $\eta_i$ to obtain a first estimated refractive index profile and estimated radius for the first half of the preform.

17. The method of claim 16, wherein the preform has a normalized radial coordinate r'=r/R, and wherein the first preform region $R_{FIT}$ is within the range $0.5 \leq r' \leq 0.98$.

18. The method according to claim 16, further including:
    defining a second preform region in the second half of deflection function that excludes the corresponding preform approximate edge;
    fitting a second target deflection function to the measured deflection function data points by varying the yet unknown radius R and yet unknown refractive index $\eta_i$ to obtain a second estimated refractive index profile for the second half of the preform; and
    combining the first and second estimated refractive index profiles to obtain final estimated refractive index profile.

19. The method according to claim 18, wherein said combining includes averaging the first and second estimated refractive index profiles.

20. The method according to claim 16, wherein said fitting is performed to within a tolerance $\delta \leq 1 \times 10^{-15}$.

* * * * *